US006183767B1

(12) United States Patent
Bessette et al.

(10) Patent No.: US 6,183,767 B1
(45) Date of Patent: Feb. 6, 2001

(54) NON-HAZARDOUS PEST CONTROL

(75) Inventors: Steven M. Bessette, Alpharetta, GA (US); Myron A. Beigler, Santa Rosa, CA (US)

(73) Assignee: Ecosmart Technologies, Incorporated, Franklin, TN (US)

( * ) Notice: Under 35 U.S.C. 154(b), the term of this patent shall be extended for 0 days.

(21) Appl. No.: 09/056,712

(22) Filed: Apr. 8, 1998

Related U.S. Application Data

(62) Division of application No. 08/870,560, filed on Jun. 6, 1997, which is a continuation-in-part of application No. 08/657,585, filed on Jun. 6, 1996, which is a continuation-in-part of application No. 08/553,475, filed as application No. PCT/US94/05823 on May 20, 1994, now Pat. No. 5,693,344, which is a continuation-in-part of application No. 08/065,594, filed on May 21, 1993, now Pat. No. 5,439,690.

(51) Int. Cl.[7] .................................................. A01N 25/32

(52) U.S. Cl. ......................... 424/406; 424/84; 424/405; 424/410; 514/546; 514/717; 514/718; 514/720; 514/729; 514/730; 514/739

(58) Field of Search ............................ 424/84, 410, 405, 424/406, 409; 514/529, 546, 717–720, 729–730, 739, 724, 762, 763

(56) References Cited

U.S. PATENT DOCUMENTS

| | | | |
|---|---|---|---|
| 4,186,103 | * 1/1980 | Hall et al. | 252/174.11 |
| 4,663,315 | * 5/1987 | Haregawa et al. | 514/86 |
| 5,118,506 | * 6/1992 | Eichoefer | 424/196.1 |
| 5,192,545 | * 3/1993 | Nakashima | 424/78.1 |
| 5,196,200 | * 3/1993 | Wilson | 424/411 |
| 5,439,690 | 8/1995 | Knight | 424/687 |
| 5,474,898 | 12/1995 | Venter et al. | 435/6 |
| 5,653,991 | * 8/1997 | Rod | 424/406 |
| 5,676,958 | * 10/1997 | Emerson | 424/405 |

FOREIGN PATENT DOCUMENTS

| | | |
|---|---|---|
| 42 31 045 A 1 | 4/1992 | (DE) . |
| WO 85/05038 | 9/1972 | (WO) . |
| WO 93/00811 | 11/1985 | (WO) . |
| WO91/17300 | * 11/1991 | (WO) . |

OTHER PUBLICATIONS

James A. Nathanson and Edward J. Hunnicutt, "N–Demethylchlordimeform a Potent Partial Agonist of Octopamine–Sensitive Adenylate Cyclase"; Molecular Pharmacology, 20:68–75; Feb. 5, 1981.

James A. Nathanson, "Phenyliminoimidazolidines Characterization of a Class of Potent Agonists of Octopamine–Sensitive Adenylate Cyclase and Their Use in Understanding the Pharmacology of Octopamine Receptors"; Molecular Pharmacology, 28:254–268; Jun. 5, 1985.

Joel M. Wierenga and Robert M. Hollingworth, "Octopamine Uptake and Metabolism in the Insect Nervous System"; Journal of Neurochemistry; Jun. 29, 1989; pp. 479–489.

(List continued on next page.)

Primary Examiner—Neil S. Levy
(74) Attorney, Agent, or Firm—Leonard Bloom

(57) ABSTRACT

A pesticide and a method of using the pesticide to kill invertebrates, especially insects, arachnids and larvae. The method is to prepare a mixture of a carrier with the pesticide and apply the mixture to the insects, arachnids and larvae and their habitat. The pesticide is a neurotransmitter affector utilizing octopamine receptor sites in the insects, arachnids and larvae. The affector agent is a chemical having a six membered carbon ring having substituted thereon at least one oxygenated functional group. The affector agent is a chemical component of a plant essential oil and is naturally occurring. Deposition of the chemicals of the present invention on a surface provides residual toxicity for up to 30 days. Various carriers for the affector agent are disclosed. The chemicals of the present invention deter feeding of insects, arachnids and larvae and also retard growth of the larvae of the insects and arachnids.

7 Claims, 5 Drawing Sheets

OTHER PUBLICATIONS

A. Guillen et al, "Ceratitis–capitata Brain Adenylate Cyclase and its Membrane Environment", Arch Biochem Biophys, vol. 286, No. 2, 1991, pp. 591–595.

A. Guillen et al, "A possible new class of octopamine receptors coupled to adenylate cyclase in the brain of the dipterous Ceratitis capitata. Pharmacological characterization and regulation of 3H–octopamine binding", Life Sci., vol. 45, No. 7, 1989, pp. 655–662.

W. Hertel et al, "The octopaminergic system of the invertebrates and its importance as insecticide target", Biol. Rundschau, vol. 27, No. 6, 1989, pp. 307–317.

A. Hirashima et al, "Effect of insecticidal cyclic phosphorthionates on adenylate cyclase and phosphordiesterase", Pesticide Biochemistry and Physiology, vol. 38, No. 2, 1990, pp. 186–195.

D.M. Soderlund et al, "Inhibition of octopamine–stimulated adenylate cyclase activity in two–spotted mites by dicofol and related diphenylcarbional acaricides", Pestic. Biochem. Physiol., vol. 46, No. 3, 1993, pp. 228–235.

Coats J R et al, "Toxicity and Neurotoxic Effects of Monoterpenoids in Insects and Earthworms", ACS Symposium Series, 1991, pp. 305–316.

JP 01 016 706 A (Mikasa Kagaku Kigyo KK), "Non–Toxic Insecticide Composition", abstract., Jan. 1989.

JP 05 039 203 A (Earth Seiyaku KK), "Safe Miticidal Compositions Having No Residual Toxicity", abstract, Feb. 1993.

JP 04 091 003 A (Jumoku Chushutsusei), Acaracide Containing Alkyl– or Aralkyl Eugenol or Isoeugenol, abstract, Mar. 1992.

JP 52 110 823 A (Takasago Perfumery Co Ltd), "Insecticides Containing a 10C Ether", abstract, Sep. 1977.

JP 02 049 703 A (Univ Kinki GH), "Insecticidal Composition for Killing Thrips Insects", abstract, Feb. 1990.

JP 04 149 103 A (Taisho Pharm Co Ltd), "Acaricidal Composition to Control Indoor Dust Mite", abstract, May 1992.

Patent Abstract of Japan, JP 04 059703, Application No. 02166735 (T. Hasegawa Co., Ltd.), abstract, Feb. 1992.

Patent Abstracts of Japan, JP 59 222402 A, Application No. 58098489 (Otsuka Kagu Kogyo KK), abstract, Dec. 1984.

* cited by examiner

NON-HAZARDOUS PEST CONTROL

CROSS REFERENCE TO RELATED APPLICATIONS

The present application is a divisional application of Ser. No. 08/870,560 filed Jun. 6, 1997, which is a continuation-in-part of application Ser. No. 08/657,585, filed Jun. 6, 1996, which is a continuation-in-part of Ser. No. 08/553,475, filed Nov. 9, 1995; now U.S. Pat. No. 5,693,344 which is, in turn the National Phase of PCT/US94/05823, filed May 20, 1994; which is in turn, a continuation-in-part of U.S. patent application Ser. No. 08/065,594, filed May 21, 1993, now U.S. Pat. No. 5,439,690.

BACKGROUND OF THE INVENTION

The present invention relates to a method of controlling pests and more particularly to a method of preparing and applying a pesticide which affects octopamine receptor sites in insects, arachnids and larvae.

Many chemicals and mixtures have been studied for pesticidal activity for many years with a goal of obtaining a product which is selective for invertebrates such as insects, arachnids and larvae thereof and has little or no toxicity to vertebrates such as mammals, fish, fowl and other species and does not otherwise persist in and damage the environment. Most products of which the applicants are aware and which have sufficient pesticidal activity to be of commercial significance, also have toxic or deleterious effects on mammals, fish, fowl or other species which are not the target of the product. For example, organophosphorus compounds and carbamates inhibit the activity of acetylcholinesterase in insects as well as in all classes of animals. Chlordimeform and related formamidines are known to act on octopamine receptors of insects but have been removed from the market because of cardiotoxic potential in vertebrates and carcinogenicity in animals and a varied effect on different insects. Also, very high doses are required to be toxic for certain insect species.

It is postulated that amidine compounds affect the octopamine sensitive adenylate cyclase present in insects [Nathanson et al, *Mol. Parmacol* 20:68–75 (1981) and Nathanson, *Mol. Parmacol* 28: 254–268 (1985)]. Another study was conducted on octopamine uptake and metabolism in the insect nervous system [Wierenga et al, *J Neurochem* 54, 479–489 (1990)]. These studies were directed at nitrogen containing compounds which mimic the octopamine structure.

Insecticides such as trioxabicyclooctanes, dithianes, silatranes, lindane, toxaphen, cyclodienes and picrotoxin act on the GABA (gamma amino butyric acid) receptor. However, these products also affect mammals, birds, fish and other species.

There is a need for a pesticide which targets only insects, arachnids and their larvae and does not produce unwanted and harmful affects on other species.

BRIEF SUMMARY OF THE INVENTION

It is a primary object of the present invention to provide a method of preparing and applying a pesticide which kills invertebrates, especially insects, arachnids and their larvae and has no harmful effects on other species including mammals, fish and fowl.

It is a further object of the present invention to provide a method of preparing and applying a pesticide which exerts its pesticidal properties through the octopamine receptor site in insects, arachnids and their larvae and other invertebrates.

It is still another object of the present invention to provide a method of preparing and applying a pesticide at relatively low concentrations which will be effective over a comparatively long period of time such as at least 24 hours.

In accordance with the teachings of the present invention, there is disclosed a method of killing insects and arachnids and larvae thereof. The steps include preparing a mixture of a carrier with an affector agent which interferes with the neurotransmitters of the octopamine receptor site in insects, arachnids and their larvae and applying the mixture to insects, arachnids, larvae and their habitat. The affector agent interacts with octopamine receptor sites in the insects, arachnids and larvae and interferes with neurotransmission in the invertebrate but does not affect mammals, fish and fowl. The agent is a chemical having the structure of a six member carbon ring, the carbon ring having substituted thereon at least one oxygenated functional group.

There is further disclosed a method of killing insects and arachnids and larvae thereof. A blend of cinnamic alcohol, eugenol and alpha terpineol is prepared. The blend is mixed with a carrier to produce a uniform mixture. The mixture is applied to insects and arachnids and larvae and their habitat. The blend interacts with octopamine receptor sites in the invertebrate and interferes with neurotransmission in the invertebrate but does not affect mammals, fish and fowl.

In another aspect, there is disclosed a pesticide which has an affector agent having a six member carbon ring. The carbon ring has substituted thereon at least one oxygenated functional group. The affector agent affects the octopamine receptor site in invertebrates including insects, arachnids and their larvae. The affector agent is intimately mixed with a carrier. Exposure of insects, arachnids and their larvae to the affector agent produces a disruption of the octopamine receptor site in the invertebrates to interfere with neurotransmission in the invertebrate and the death of the exposed invertebrate.

Further disclosed is a method of killing insects, arachnids, and larvae. A mixture is prepared of a chemical derived from a plant essential oil with a carrier. The chemical has at least one oxygenated functional group therein. The chemical has octopamine receptor site inhibitory activity. The mixture is applied to insects, arachnids, larvae and their habitat. The chemical interacts with an octopamine receptor site in the insects, arachnids and larvae and interferes with neurotransmission in the insects, arachnids and larvae thereof but does not affect mammals, fish and fowl.

In another aspect there is disclosed a method of controlling insects, arachnids and their larvae. An emulsion is prepared of an affector agent which disrupts neurotransmission at the octopamine receptor site in insects, arachnids and their larvae. The mixture is applied to insects, arachnids, larvae and their habitat. The agent interacts with octopamine receptor sites in the insects, arachnids and larvae and deters the feeding of the insects, arachnids and larvae but does not affect mammals, fish and fowl.

In yet another aspect there is disclosed a method of controlling insects, arachnids and larvae. An affector agent mixed with a carrier is applied to larvae of the insects and arachnids and their habitat. The affector agent retards the growth of the larvae. The affector agent interacts with octopamine receptor sites in the larvae of the insects and arachnids and interferes with neurotransmission in the larvae but does not affect mammals, fish and fowl. The affector agent is a naturally occurring organic chemical having at least six (6) carbon atoms.

In addition, there is disclosed a method of killing insects, arachnids and larvae thereof. A mixture is prepared of a carrier and a naturally occurring organic chemical having at least six carbon atoms. The chemical has octopamine receptor site inhibitory activity. The mixture is applied to insects and arachnids and larvae thereof and their habitat. The chemical interacts with an octopamine receptor site in the insects and arachnids and larvae thereof and interferes with neurotransmission in the insects, arachnids and larvae thereof but does not affect mammals, fish and fowl.

These and other objects of the present invention will become apparent from a reading of the following specification, taken in conjunction with the enclosed drawings.

DESCRIPTION

Figure 1:
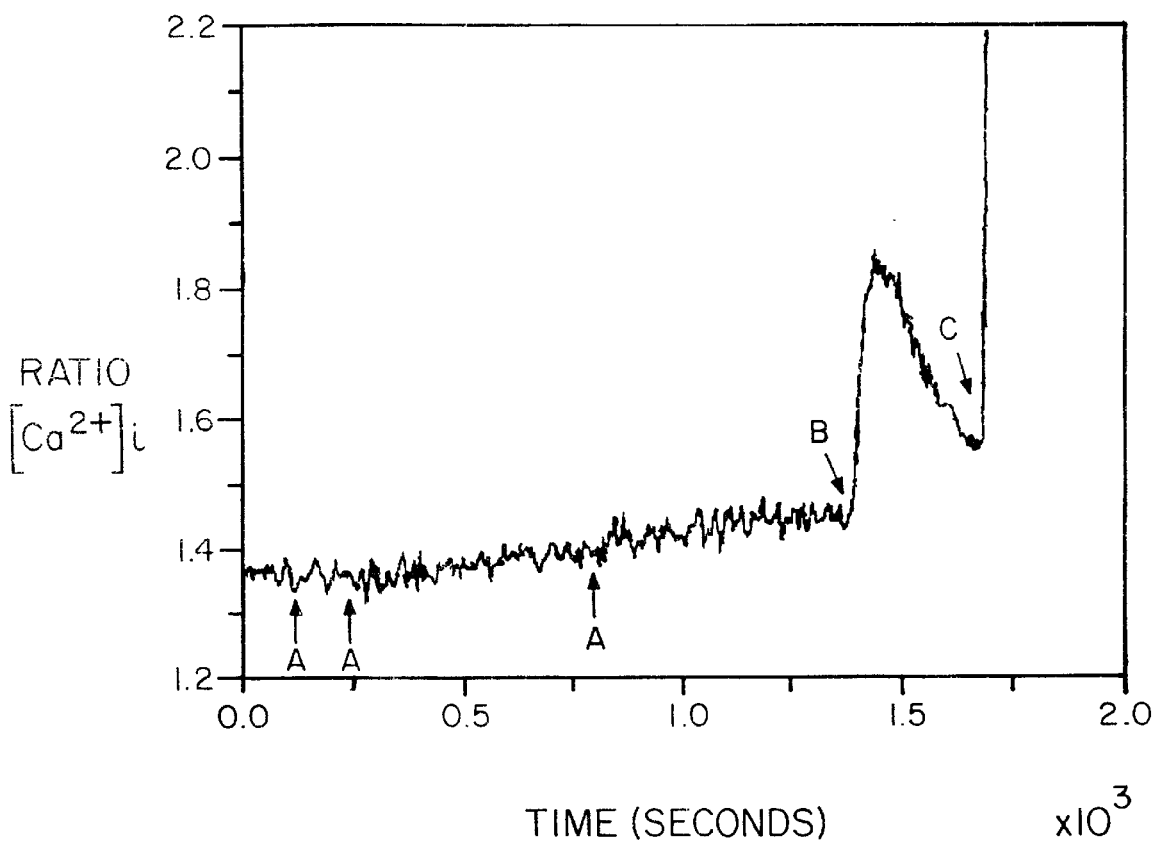
FIG. 1 is a graph showing the effect of the 3-B mixture of the present invention on the intracellular concentration of [$Ca^{2+}$] in neuronal cells.

Physiological activity to invertebrate insects, arachnids and their larvae are produced by the chemicals of the present invention and by mixtures of these chemicals. The following chemicals having a six member carbon ring and having substituted thereon at least one oxygenated functional group are representative of the chemicals of the present invention but these are not to be considered as being the totality of chemicals and are not a limitation.

| trans-anethole | 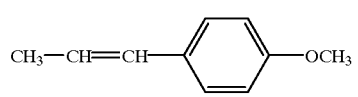 |
| benzyl acetate | 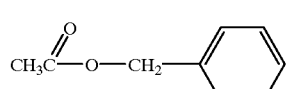 |
| benzyl alcohol | 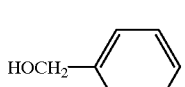 |

| carvacrol | 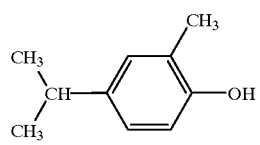 |
| cinnamic alcohol | 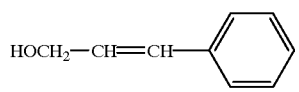 |
| eugenol | 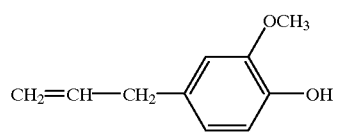 |
| phenyl ethyl alcohol | 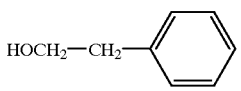 |
| pulegone | 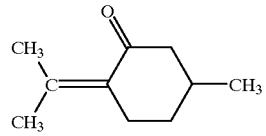 |
| alpha-terpineol | 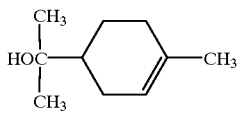 |
| thymol | 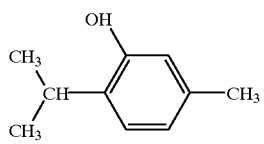 |

The above-listed materials are all components of plant essential oils. A further plant essential oil which is a chemical of the present invention is

| citronellal | 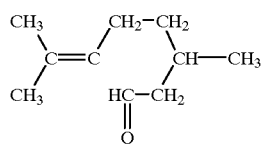 |

Anethole, carvacrol, citronellal, eugenol, D-pulegone, alpha-terpineol and thymol are all monoterpenes each having ten (10) carbon atoms therein.

The present invention is not limited to the chemicals listed herein.

All of the chemicals of the present invention are naturally occurring organic chemicals which are devoid of halogens. Further, several of the chemicals of the present invention are considered by the U.S. Environmental Protection Agency (EPA) to be safe for humans and exempted from registration. Thus, these chemicals do not require prior approval or registration with the EPA. Some of these chemicals have been added to prior art insecticides as attractants and repellents. However, there have been no reports of these chemicals having toxic pesticidal activity at the concentrations disclosed in the present invention.

All of the chemicals of the present invention act as agonists or antagonists on the octopamine receptor site in insects, arachnids and their larvae and, consequently, produce physiological effects in exposed invertebrates. The chemicals of the present invention are considered to be affector agents. Exposure to reduced concentrations of the chemicals or exposure for brief times affect the feeding habits of the exposed insects, arachnids and larvae. This is important in those invertebrates which feed on vegetation, since there is reduced damage to plants by invertebrates which have received sublethal concentrations of the chemicals of the present invention. Also, the insects, arachnids or larvae which survive exposure to the chemicals of the present invention are shown to be stunted in growth.

Alpha-terpineol, eugenol and cinnamic alcohol were dissolved in acetone and designated as sample 3B. The range of weight percentages of the components of the blend are alpha-terpineol 10%–50%, eugenol 10%–50% and cinnamic alcohol 20%–35%. The preferred blend has equal parts by weight of each of the components. Male and female American cockroaches were injected with 3B into the abdomen. Overt signs of toxicity were observed at 1 mg/roach in 2 $\mu l$ of acetone. At lower doses no symptoms were observed. By this approach, 2 out of 6 died within 30 minutes. For those surviving, some showed locomotive difficulties. No hyperactivity was observed, even in those that died quickly. In some cases, (2/6) treated insects died after 2 to 3 days.

None of the American cockroaches died when they were treated through topical application prior to 24 hours. A 40% (4/10) mortality was observed 24 hours after treatment and this effect was time dependent. After 72 hours, 100% died. Control insects receiving 2 $\mu l$ of only acetone through injection showed no ill effects (Table 1).

TABLE 1

Time course effect of 3-B (1 mg/insect) on American cockroaches treated by topical application.

| Time (hr.) | Mortality-3B | Mortality-Control |
| --- | --- | --- |
| 24 | 4/10 | 0 |
| 48 | 6/10 | 0 |
| 72 | 10/10 | 0 |

The data from the above study suggests that the action of 3B depends on the site of application, i.e., abdominal injection vs. topical application for the whole body.

3B was applied to different areas of the insect. When given to the ventral sternum region (at the base of the hind legs) of the American cockroach, 3B was most toxic at 125 $\mu g$/insect. In that case, overt toxic signs were observed within 10 minutes. A lethal dose of 250–500 $\mu g$/insect was injected and the insects died within 30 minutes (Table 2).

TABLE 2

Time-course and dose-response of 3B on American cockroaches treated by injection through the ventral stenum.

| Time | Mortality Test Doses $\mu g$/insect | | | | |
| --- | --- | --- | --- | --- | --- |
| (hrs.) | 50 | 100 | 125 | 250 | 500 |
| 0.5 | 0 | 2/10 | 6/10 | 10/10 | 10/10 |
| 1.0 | 2/10 | 3/10 | 7/10 | — | — |
| 1.5 | 5/10 | 7/10 | 9/10 | — | — |
| 2.0 | 5/10 | 9/10 | 10/10 | — | — |
| 3.0 | 6/10 | 9/10 | — | — | — |
| 5.0 | 8/10 | 10/10 | — | — | — |
| 24.0 | 10/10 | — | — | — | — |

*No mortality was found in insects treated exactly in the same manner with equal volume of acetone (vehicle) alone as control.

In the latter case of injection of a lethal dose the hind legs appeared to be paralyzed and the fore and mid legs moved rapidly, although there was no overt hyperexcitation. This phenomenon of quick death was also observed in German cockroaches that were treated through topical application (3B is more toxic to German than to American cockroaches). At 125 $\mu g$/insect, 80% (8/10) of German cockroaches were knocked down in 2 to 3 hours and died within 24 hours (dose was 125 $\mu g$ 3B per insect with 0.4 $\mu l$ acetone).

The above data support the observation that site of application gives varying degrees of toxicity. For further confirmation, 1 mg 3B in 20 ml acetone was applied to small jars and all surfaces were covered. One hour after the acetone had completely evaporated, 5 American cockroaches were introduced to each jar. Control jars were treated exactly as above but with 20 ml acetone only. All cockroaches died within 10 to 30 minutes in the jars containing 3B. None died in the control jars. Some insects (3/5) showed hyperactivity within 1 to 3 minutes after exposure. At 8 minutes, hind leg paralysis was observed. These "walk across" data are consistent with the previous study in which a rapid death was observed when 3B was given to the ventral sternum region rather than the abdomen. The fact that the toxicants might penetrate faster through the legs (no chitin layer as in the body) support the notion that the permeability/penetration of 3B plays a key role in its toxicity (Table 3).

TABLE 3

Time-course effect of 3B (1 mg/jar) on American cockroaches exposed to pre-treated surface one hour after 3-B application.*

| Time (min.) | Mortality |
| --- | --- |
| 10 | 3/5 |
| 15 | 3/5 |
| 20 | 4/5 |
| 30 | 5/5 |

*No death in insects exposed to surface treated with acetone alone.

Based on these data, the same treated jars were used for a residual study. In this experiment, American cockroaches were transferred to the treated and control jars at different times from the point in time at which acetone evaporated, i.e., 24, 48, 96, 72 hours and 7 days. Interestingly, all insects died after being exposed to treated jars, even 7 days after 3B application. However, it took longer for the roaches to die in proportion to the length of time from initial 3B application to the jar. Some toxic signs were observed in all cases after exposure. Further, when the same experiment was repeated with German cockroaches, greater toxic effects and more rapid effects were observed. It appears that some degradation occurs in toxic effects with time (Table 4).

TABLE 4

Effect of 3-B (1 mg/jar) when applied to surfaces on American cockroaches exposed to these surfaces at different times after surface treatment.

| Time elapsed after 3-B application (days) | Time required to kill 100% of insects (days) |
| --- | --- |
| 1 | 1 |
| 2 | 3 |
| 3 | 6 |
| 5 | 8 |
| 7* | 10 (6/10 died) |

*Only 6 insects died when 10 cockroaches were exposed to pretreated jars 7 days after 3-B application.

The toxic effects shown in Table 4 could be protracted by combining oils with different characteristics. Eugenol, one of the ingredients of 3-B, was dissolved in galoxolide, a perfume oil that imparted longer lasting properties related to evaporation and oxidation to the pesticide properties of eugenol. Mixtures having 30%–60% galoxolide and 40%–70% eugenol by weight have been effective. As an example, eugenol and galoxolide were mixed in equal parts, 1 mg each, in 10 ml of acetone and agitated vigorously for two minutes and then applied (1 mg of mixture/jar) as above to small jars and all surfaces covered. The data of this example (Table 5) show that the lethal effect of the mixture was extended and enhanced.

TABLE 5

| Time elapsed after eugenol/galoxolide* application (weeks) | Time required to kill 100% of insects (days) |
| --- | --- |
| 1 | 1 |
| 2 | 1 |
| 3 | 1 |
| 4 | 1 |

*1, 3, 4, 6, 7, 8-hexahydro-4, 6, 6, 7, 8, 8-hexamethyl-cyclopentagamma-2-benzopyran Cockroach abdominal nerve cord showed the second highest uptake of octopamine of all tissues studied [J. Neurochem 54 479–489 (1990)]. The high efficacy of the chemicals of the present invention in the "walk across" study is attributed to the high concentration of octopamine receptors on the ventral nerve cord in close proximity to the hind legs.

Since the toxic signs produced by 3B did not indicate cholinergic action patterns, other major possibilities such as GABA receptor, octopamine receptor/biogenic amine binding, $[Ca^{2+}]$, or mitochondrial respiratory poison were considered:

1. GABA receptor-chloride channel study: This site of action is known to be one of the major action sites for a number of insecticides. When the action of 3B was tested, 3H-EBOB ($[^3H]$n-propyl bicyclo ortho benzoate) and 35S-TBPS (bicyclo phosphorous esters) were used. The former ligand was used based on the findings that EBOB has been shown to be both a highly toxic and high affinity radioligand for the GABA-receptor convulsant binding site in insects. It also shows identical or overlapping binding sites with seven classes of insecticides: trioxabicyclooctanes, dithianes, silatranes, lindane, toxaphen, cyclodienes and picrotoxinin. The TBPS has been hindered by poor toxicological relevance and binding affinity in insects. Both radioligands were used in this study for comparison. As shown in Table 6, 3B induced no antagonistic action on the binding affinity of 3H-EBOB or 35S-TBPS at concentrations of 3B ranging from 10 $\mu$M to 10 NM. Only at 100 $\mu$M was a significant effect seen. However, at such a high concentration (100 $\mu$M), the specificity for the site of action is unlikely. In contrast, heptachlrepoxide alone and a mixture of Endosulfan I (60%) and Endosulfan II (40%) as a positive standard were highly active even at 10 Nm. These data indicate that this assay system works poorly with 3B, and that the lack of its action is due to its inaccessibility to the GABA receptor site. The fact that the cyclodiene resistant London strain showed cross-resistance to 3B supports the above data and rules out GABA receptor as the target or site of action for 3B.

TABLE 6

Effect of 3B on GABA-receptor binding.

| Tested Concentration ($\mu$M) | dpm per 200 $\mu$g synaptosomal membrane protein (X ± SD) | |
| --- | --- | --- |
| | $^3$H-EBOB | $^{35}$S-TBPS |
| 3-B ($\mu$M) | | |
| 0 | 2558 ± 159 | 3361 ± 297 |
| 0.01 | 2069 ± 98 | 2991 ± 101 |
| 0.10 | 2069 ± 198 | 2939 ± 111 |
| 1.0 | 2088 ± 76 | 2917 ± 85 |
| 10 | 2111 ± 151 | 3001 ± 173 |
| 100 | 2109 ± 88 | 2985 ± 203 |
| Endosulfan Mix $\mu$M | | |
| 0 | 2558 ± 159 | 3361 ± 297 |
| 0.01 | 1886 ± 71 | 2477 ± 162 |
| 0.1 | 1009 ± 83 | 1358 ± 101 |
| 1.0 | 350 ± 35 | 552 ± 43 |
| 10 | 255 ± 29 | 360 ± 15 |
| 100 | 241 ± 18 | 285 ± 11 |
| Hepatachlorepoxide $\mu$M | | |
| 0.001 | 2010 ± 91 | 2470 ± 188 |
| 0.01 | 1583 ± 77 | 2000 ± 75 |
| 0.10 | 1221 ± 63 | 1699 ± 109 |
| 1.0 | 1142 ± 85 | 1493 ± 99 |
| 10 | 591 ± 41 | 685 ± 66 |
| Unlabeled Ligand $\mu$M | | |
| 0.001 | 499 ± 34 | 533 ± 25 |
| 0.01 | 346 ± 29 | 381 ± 17 |
| 0.10 | 206 ± 15 | 211 ± 19 |

Control value (solvent alone) was 2558 ± 159 × 3361 ± 297 for EBOB × TBPS, respectively.

2. Octopamine receptor/biogenic amine binding site: Biogenic amines are known to carry out a number of physiological functions through their specific receptors in insects. The octopamine receptor is the most dominant biogenic amine receptor in insects. Certain acaricides, such as chlordimeform, are known to act on octopamine receptors, causing a variety of symptoms, including behavioral changes. When 3B was incubated directly with a homogenate of the nerve cord of American cockroaches, a significant increase in cylical AMP (Camp) was found at a dosage of 1 $\mu$M. The chemical octopamine was used as a positive control and induced a significant increase in Camp at 1 $\mu$M.

Additional evidence that octopamine is the main site of action of 3B is that in co-treatment of 3B and octopamine, 3B abolished the octopamine-induced increase in cAMP.

To confirm that 3B is an octopamine receptor toxicant, two important biomarkers were measured: heart beats/30 seconds and cAMP-dependent protein kinase (PKA) activity. These two are considered particularly important in identifying octopamine receptor activity as the cockroach heart has been shown to have a high concentration of octopamine receptors. When a 200 μg/insect concentration of 3B was applied to the sternum region of the alive and intact American cockroach, a significant increase was seen in heart beats/30 seconds and this was accompanied with an increase in cAMP. As before, higher concentrations of 3B resulted in a decrease in heart beats (Table 7).

TABLE 7

Effect of 3-B on American cockroach heart beats/30 seconds.

| Tested Doses, μg | Before Treatment | 30 Min. After Treatment |
| --- | --- | --- |
| control | 55 ± 1.9 | 55 ± 3.2 |
| 200 | 55 ± 2.1 | 71 ± 4.5 |
| 300 | 58 ± 0.81 | 67 ± 1.63 |
| 600 | 57 ± 0.47 | 41 ± 2.4 |
| 900 | 53 ± 1.9 | 38 ± 2.8 |
| octopamine (20 μg) | 54 ± 2.1 | 75 ± 3.6 |
| chlordimeform (20 μg) (positive control) | 51 ± 1.4 | 69 ± 2.5 |

In addition, when 3B was incubated with synaptasomal preparation from American cockroach heads, a significant increase in PKA activity was found, which is consistent with the above conclusion (Table 7).

TABLE 8

In Vivo effect to 3-B (200 μg/roach) on the activity of PKA in synaptosomal membrane of American cockroaches.

| | dpm/1 nmol of Kemptide/5 min. X ± SD |
| --- | --- |
| Control | 1753 ± 57 |
| 3-B | 4008 ± 201 |

3. Possible role of [$Ca^{2+}$]: Because of the locomotive difficulties noticed among cockroaches treated with 3B at the ventral sternum region, it was postulated that increases in intramuscular levels of $Ca^{2+}$ could be involved in the contractions of hind legs. For this purpose, mammalian cell line PC12 rat chromaffin adrenal cells was used. This cell line is known to mimic neuronal cells, particularly catecholaminergic neurons and has been used as a model for $Ca^{2+}$ induced presynaptic transmitter release phenomena. As shown in FIG. 1 when 3B was added at 100 μM to these cells (at A), there was no change in intracellular free $Ca^{2+}$. [$Ca^{2+}$] concentration inside PC12 cells was found using spectrofluorometric measurements with Fura 2/AM (a cell penetrating fluorescence probe for free $Ca^{2+}$). A standard positive control, thapsigargin clearly increased the [$Ca^{2+}$]i (at B) even at 500 Nm. Also, 10 μM ionomycin, a $Ca^{2+}$-ionophore (at C) produced the expected increase of $Ca^{2+}$ entry. These results showed that 3B shows no ability to regulate any type of calcium homeostasis in mammalian cells.

The effect of the chemicals of the present invention on the rat brain tissue cells was as follows where cyclical AMP generation is measured as dpm/mg protein

| control | 5395 ± 43 |
| --- | --- |
| 3-B | 5411 ± 391 |
| terpineol | 5399 ± 219 |
| eugenol | 5461 ± 488 |
| phenyl ethyl alcohol | 5499 ± 415 |

Thus, no change was produced in the neurotransmission system of a mammal. These data confirm the lack of neurotoxicity of these essential oils in mammals.

4. Mitochondrial/respiratory poison: Another possible mode of action is that of mitochondrial or respiratory poisoning. It has been observed that all mitochondrial poisons induce hyperactivity at some point in their action. However, when American cockroaches were treated with a topical application of 3B, no hyperactivity or hyper excitation was observed at any stage of poisoning at all concentrations used. On the other hand, when American cockroaches were exposed to pre-coated jars with 1 mg of a 60% solution of 3B, the insects showed hyper excitation. These data suggest that the mode of entry is a determining factor in the mode of action of these essential oils. These observations support the idea that 3B is not a type of poison that attacks the Nag channel as a main target. The fact that the Kdr-resistant strain (with a mutated $Na^+$ channel making it insensitive to DDT and pyrethroids) did not show cross-resistance to 3B also supports this diagnosis.

Under the above circumstances, where all of the known major sites of action for insecticides were found to be insensitive to 3B, except the antagonistic effect on the octopamine receptor, the possibility was considered that the mode of action of this group of chemicals is totally novel.

Figure 2:
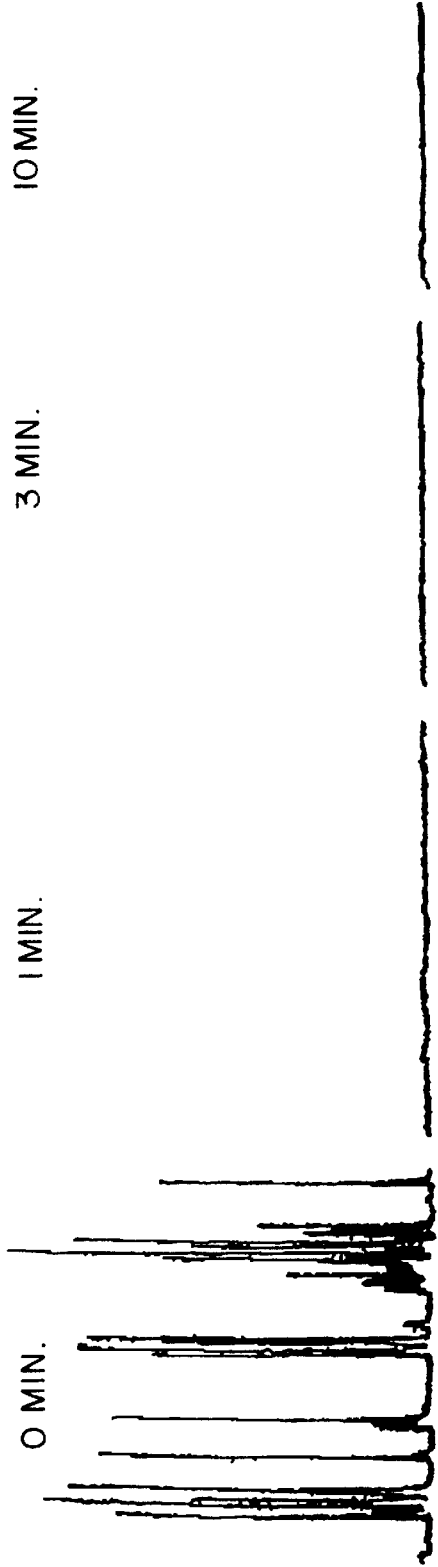
FIG. 2 is a chart showing the contraction of cockroach leg muscles induced by electrical stimulation when the 3-B mixture of the present invention is injected into the thorax of a live cockroach.
Figure 3:
FIG. 3 is a chart showing the contraction of cockroach leg muscles in an isolated leg induced by electrical stimulation when the 3-B mixture of the present invention is applied to the isolated leg.
Figure 4:
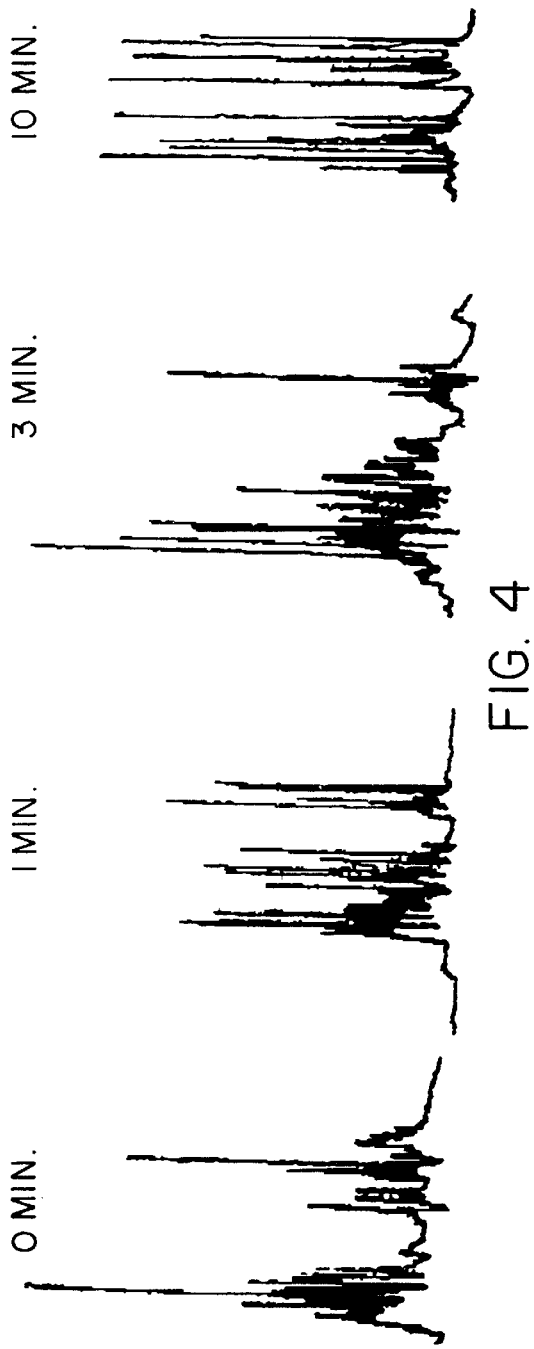
FIG. 4 is a chart showing the test of FIG. 2 using acetone as a control without the 3-B mixture.
Figure 5:
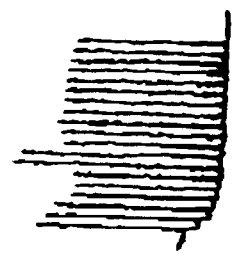
FIG. 5 is a chart showing the test of FIG. 3 using acetone as a control without the 3-B mixture.
Figure 6:
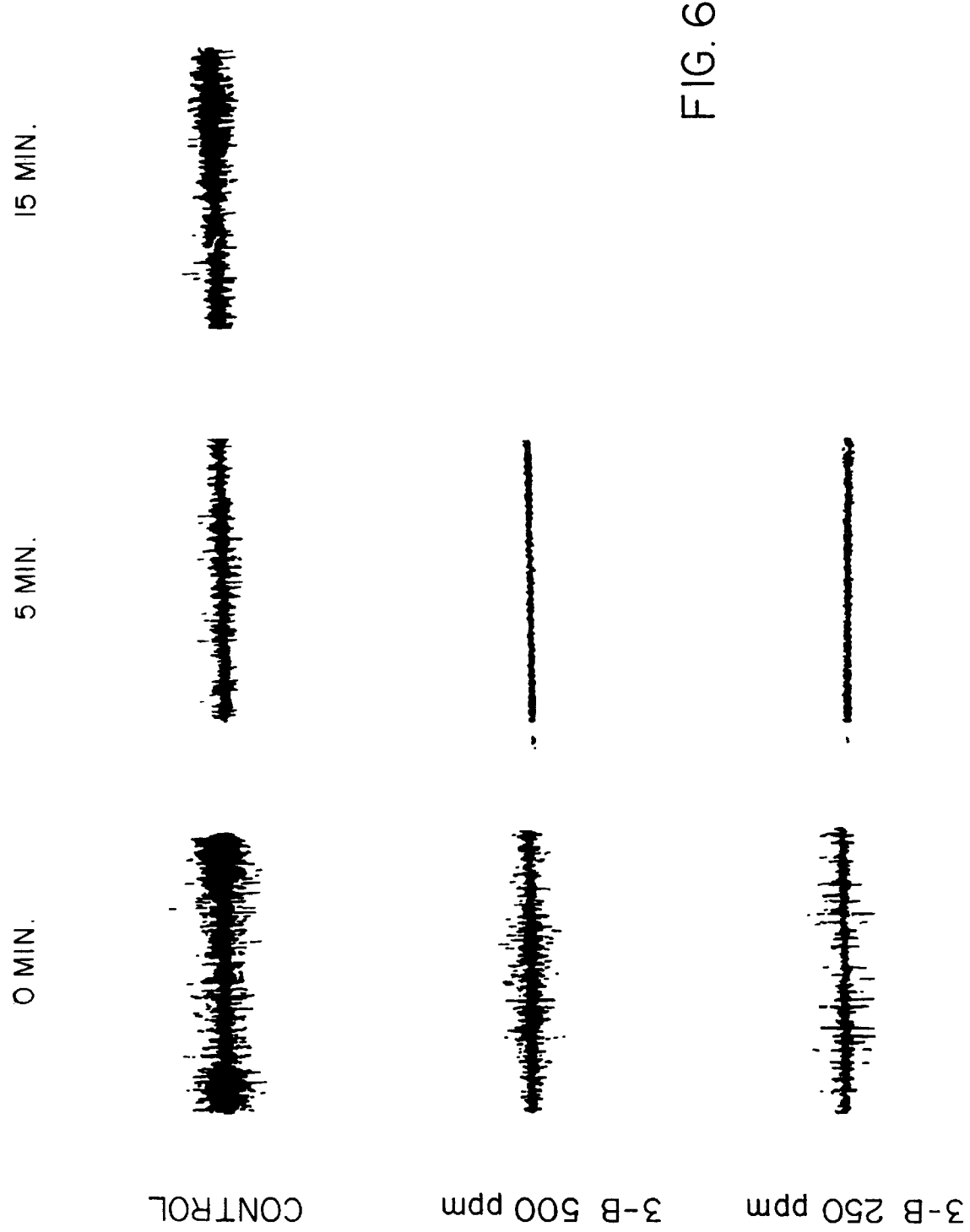
FIG. 6 is a series of charts showing transmission of signals from the mechanoreceptors of the cerci after application of the 3-B mixture and a control to the abdominal nerve of the cockroach.

It was noted that the toxicity of 3B varies according to the site of application, at least in the case of the American cockroach. Such an observation indicates that 3B is likely to be not so systemic in action, and if one site produces a high toxicity, its target is likely to be located very close to that site of application. In view of the locomotive difficulty observed in American cockroaches treated at the central sternum, it was reasoned that the thoracic ganglia could be affected. When 3B (250 mg. in 0.4 μl acetone) was injected into the thorax of an alive cockroach and its hind leg contractions were induced by an external electrical stimulus applied to the outside of the body, the ability of the leg muscles to respond to stimuli totally disappeared within one minute (FIG. 2). When 3-B was applied to the leg in isolation by directly giving electrical stimuli, no effect of 3B was found (FIG. 3). These data suggest that the effect of 3B is on the nervous system and not on the muscles. Control tests using acetone (0.4 μl) without any 3-B showed no effects (FIGS. 4 and 5). This possibility was further tested using the $6^{th}$ abdominal ganglion and studying transmission of signals from the mechanoreceptors of the cerci generated by air puffing. For this purpose, the abdominal cavity was opened, exposing the entire abdominal nerve cord. A suspension solution of 3B in 200 μl insect saline was directly applied to the entire abdominal nerve cord. The results were drastic, producing complete blockage of transmission at 250–500 PPM within 5 minutes from the time of application (FIG. 6). Even at 10 PPM the blocking effect of 3B was apparent, producing visible effects in 15 minutes. These results clearly indicate that 3B is a nonsystemic nerve blocker.

A further study was conducted on the cockroach to determine the effect of other chemicals of the present invention on the heart rate of the insects. The experiment conditions were as previously described in applying 300 μg of the respective chemical to the entire abdominal nerve cord. Each insect group was comprised of three individuals. All heart rates were observed and counts were recorded three times for each individual, i.e., nine counts before introduction of the chemical, and nine counts 30 minutes after application of approximately 300 μg of chemical. The data from these heart beat tests agreed with the previously described "walk-across" test. The following chemicals showed measurable change in heart rate thirty (30) minutes after application of the chemical: terpineol, eugenol, phenyl ethyl alcohol, benzyl acetate and benzyl alcohol.

Also the following mixtures showed measurable change in heart rate: terpineol with eugenol, terpineol with phenyl ethyl alcohol and eugenol with phenyl ethyl alcohol.

The toxicity of the individual chemicals was also determined by topical application to early $4^{th}$ instar Asian armyworms (*Spodoptera litura*) (15–20 mg live wt) and measurement after 24 hours (Table 9).

TABLE 9

Toxicity of chemicals of the present invention.

| Compound | LD50 (μg/larva) | 95% confidence interval | LD90 (μg/larva) | 95% confidence interval |
| --- | --- | --- | --- | --- |
| α-terpineol | 156.0 | 148.7–163.7 | 206.4 | 190.4–249.9 |
| eugenol | 157.7 | 149.9–165.8 | 213.0 | 194.8–263.3 |
| cinnamic alcohol | LD50 > 250 | | | |
| (+)-terpinen-4-ol | 130.4 | 121.8–139.5 | 205.8 | 180.2–283.8 |
| (−)-terpinen-4-ol | 122.9 | 108.1–139.7 | 276.0 | 202.4–583.9 |
| carvacrol | 42.7 | 37.7–48.3 | 73.8 | 55.7–142.0 |
| D-pulegone | 51.6 | 49.0–54.4 | 69.7 | 62.3–91.3 |
| t-anethole | 65.5 | 61.7–69.6 | 98.8 | 88.4–129.1 |
| thymol | 25.5 | 22.9–28.3 | 46.8 | 38.5–74.5 |
| citronellal | 111.3 | 103.9–119.1 | 153.4 | 130.8–223.5 |

In establishing the LD50 dose, it was noted that all larvae treated with pulegone, even at the lowest doses tested, were almost immediately paralyzed. However, at lower doses, many or most of these larvae overcame this effect, whereas at higher doses larvae succumbed. To determine if the observed sublethal toxicity resulted in any long-term effect, subsequent growth of larvae treated at the three lowest doses (20, 31 and 49 μg per larvae) was monitored and compared this to growth of control (untreated larvae) at 72 and 100 hours after treatment (Table 10).

TABLE 10

Growth of larvae exposed to chemicals of the present invention.

| | Control | 20 μg/larva | 31 μg/larva | 49 μg/larva |
| --- | --- | --- | --- | --- |
| Mortality (5) | 0 | 0 | 2 | 52 |
| Live wt. - 72 hr. | 148 mg. | 109 | 81 | 52 |
| Live wt. - 110 hr. | 363 mg. | 289 | 248 | 163 |

The results indicate that subsequent larval growth of survivors of the highest dose is dramatically retarded. More importantly, the effect is also seen (and significantly so) at the two lowest doses, which themselves produced almost no mortality. Therefore, exposure to even sublethal doses can have significant consequences for larvae.

Dry powder formulations were prepared using the chemicals of the present invention. The examples listed below are for the 3B mixture as previously described (cinnamic alcohol, eugenol and alpha terpineol). However, these examples are for illustrative purposes only and do not limit the range of active chemicals. Other mixtures and individual chemicals may also be used. Suggested mixtures are phenyl ethyl alcohol, benzyl alcohol, eugenol and alpha terpineol (3C) and benzyl acetate, benzyl alcohol, phenyl ethyl alcohol, cinnamic alcohol and alpha terpineol (3D). The mixtures listed herein are not limiting but are typical and the present invention is not limited to these mixtures.

The procedure was to place the powder components into a 500 ml dish and apply the chemical (usually a liquid) on the powder. The powder and chemical mixed in the container were placed on an electric tumbler to dry for approximately 30 minutes. Approximately 1 cc of the resulting dry powder was applied to a Whatman No. 1 filter paper in a 9 cm Petri dish. The dust was spread evenly with a camel hair brush. A control was used which consisted only of the powder components without the chemical of the present invention.

The following compositions were prepared: (Tables 12a–12c)

TABLE 12a

| % by weight | amount | components |
| --- | --- | --- |
| 40 | 20 gr | diatomaceous earth |
| 20 | 10 gr | calcium carbonate |
| 20 | 10 gr | sodium bicarbonate |
| 10 | 5 gr | Hi-Sil 233 |
| 10 | 5 gr | active ingredient* |

*active ingredient was a mixture of the chemicals of the present invention.

TABLE 12b

| % by weight | amount | components |
| --- | --- | --- |
| 40 | 20 gr | diatomaceous earth |
| 23 | 11.5 gr | calcium carbonate |
| 20 | 10 gr | sodium bicarbonate |
| 10 | 5 gr | Hi-Sil 233 |
| 7 | 3.5 gr | active ingredient* |

*active ingredient was a mixture of the chemicals of the present invention.

TABLE 12c

| % by weight | amount | components |
| --- | --- | --- |
| 40 | 20 gr | diatomaceous earth |
| 25 | 12.5 gr | calcium carbonate |
| 20 | 10 gr | sodium bicarbonate |
| 10 | 5 gr | Hi-Sil 233 |
| 5 | 2.5 gr | active ingredient* |

*active ingredient was a mixture of the chemicals of the present invention.

The mixtures were tested by placing ten (10) common fire ants within respective Petri dishes which were then covered. The time for irreversible knockdown (KD) to occur (KT) was determined from periodic irregular observations. The insects were considered KD when they were on their back, or could be turned onto their back and could not right themselves within at least two (2) minutes. KT-50 and KT-90 (time for 50% and 90% KD respectively) were calculated by interpolation of KD between times when data was collected. The 10% mixture (Table 12a) had a KT 50% of 5 min. 50 sec. and a KT 90% of 6 min 40 sec. For the 7% mixture (Table 12b) KT 50% was 3 min. 40 sec. and KT 90% was 4 min. 40 sec. The 5% mixture (Table 12c) had KT 50% of 2 min. 33 sec. and KT 90% of 3 min. 45 sec.

The above data are examples which clearly demonstrate the effectiveness of the mixture of chemicals over concentrations ranging from 5%–10% by weight of the active ingredients. These are typical examples, but are not limiting. Concentrations as low as 0.1% by weight have also been shown to be effective for some individual chemicals and for various mixtures of chemicals. Also much higher concentrations can be used.

As an example of a high concentration, a emulsifiable concentrate has the following formulation:

| Ingredient | Purpose | wt. % |
|---|---|---|
| 3B | active ingredient | 90.0 |
| Sodium dodecyl benzene sulfonate | emulsifier | 6.6 |
| Sodium C12–15 Pareth-3 sulfonate | emulsifier | 2.0 |
| POE 20 Sorbitan Monooleate | emulsifier | 1.4 |

Another emulsifiable concentrate is:

| Ingredient | Purpose | wt. % |
|---|---|---|
| 3B | active ingredient | 90.0 |
| Caster oil (40 mol EO) | emulsifier | 10.0 |

The concentrate is diluted with up to 50 to 70 parts of water to 1 part of concentrate to provide an effective aqueous medium. Although these examples are for the 3B and 3C mixtures, the formulation is not so limited and an emulsifiable concentrate may be prepared from any of the individual chemicals of the present invention or any combination of mixtures of the individual chemicals.

The emulsifiable concentrate 3B mixture was diluted in tap water and sprayed onto cabbage and bean plants to assess efficacy against Asian armyworms and two-spotted spider mites (*Tetranychus urticae*) respectively. All values are based on a minimum of four doses with five replicates and ten armyworms or thirty adult and/or deutonymph mites per replicate. Values reported represent the ratios of water to formulation (i.e., dilution rate) (e.g., LD50 of 46.8 means a ratio of water to emulsifiable concentrate of 46.8:1). Mortality was assessed at 24 hours (Table 13).

TABLE 13

| Mortality of emulsifiable mixture of 3-B mixture | |
|---|---|
| 3-day old Asian armyworm | LD50 (95% C.I.) = 46.8 (44.0–49.8) |
| | LD90 (95% C.I.) = 30.6 (27.2–40.7) |
| 5-day old Asian armyworm | LD50 (95% C.I.) = 53.0 (49.6–56.7) |
| | LD90 (95% C.I.) = 33.7 (29.7–45.6) |
| two-spotted spider mite | LD50 (95% C.I.) = 82.3 (76.5–88.5) |
| | LD90 (95% C.I.) = 55.9 (49.3–75.5) |

Figure 7:
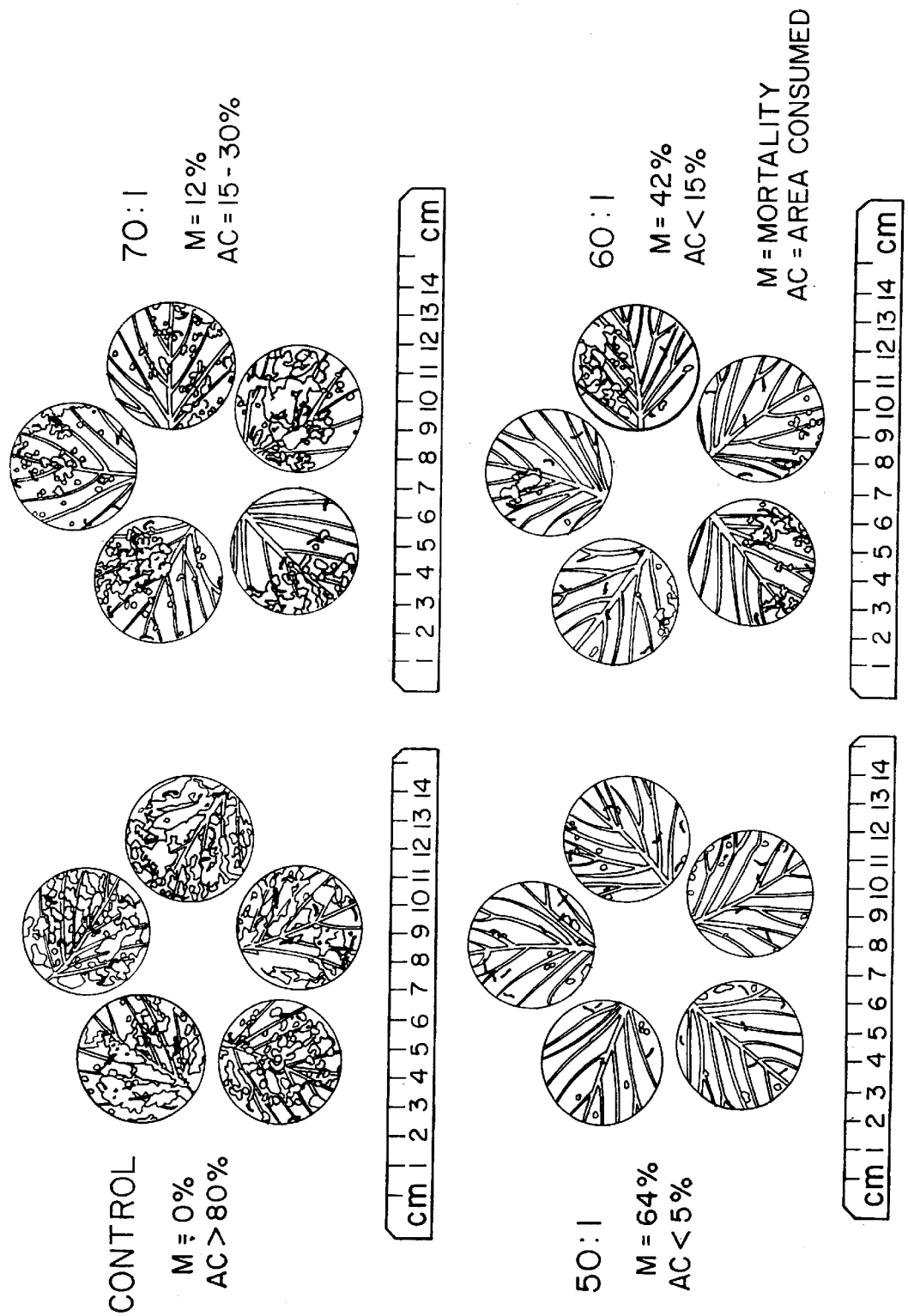
FIG. 7 is a chart showing feeding damage to cabbage plant leaf discs with the 3-B mixture as compared to a control.

The diluted emulsifiable concentrate 3B formulation shows good efficacy against both ages of armyworms, and even better efficacy against spider mites. Five-day old armyworms are approximately the same size as mature (last instar) diamondback moth larvae, a potential target species. Also of importance, it was observed that sublethal concentrations clearly deter feeding and therefore plant damage. At a dilution of 50:1, 60:1 and 70:1, larval mortality is only 64%, 42% and 12% respectively. However, there is minimal feeding damage from surviving larvae. As shown in FIG. 7, discs of cabbage plant leaves with 3-B emulsifiable concentrate diluted 50:1, 60:1 and 70:1 have areas consumed (ac) after 24 hours of less than 5%–30% as compared to a control (without 3-B) of greater than 80% area consumed.

Another example of a high concentration is a wettable powder having the following formulation:

| Ingredient | Purpose | wt. % |
|---|---|---|
| 3B | active ingredient | 50.0 |
| Silica, hydrated, amorphous | absorbent | 41.5 |
| Sodium alkyl naphthalene sulfonate | dispersant | 3.0 |
| Sodium dioctyl sulfosuccinate | wetting agent | 0.5 |
| Sodium dodecyl benzene sulfonate | emulsifier | 5.0 |

One part of this powder is mixed with up to 30–50 parts of water to provide an effective pesticide. This example is for the 3B mixture but is not limited and may be prepared with any of the individual chemicals of the present invention or any combination of mixtures of the individual chemicals.

A waterproof dust may be prepared using any of the individual chemicals or a mixture of any of the chemicals of the present invention. The following formulation is representative in which the mixture 3C is equal parts by weight of benzyl alcohol, phenyl ethyl alcohol and terpineol:

| Ingredient | Purpose | wt. % |
|---|---|---|
| 3C | active ingredient | 5.0 |
| Diatomaceous earth | bulking agent | 75.0 |
| Hydrophobic silica | absorbent | 20.0 |

The following formulations represent two ready to use sprays representative of mixtures 3B and 3C but may be used for other mixtures and for individual chemicals of the present invention:

| Ingredient | Purpose | wt. % |
|---|---|---|
| 3B | active ingredient | 5.0 |
| Caster oil (40 mol EO) | emulsifier | 2.7 |
| POE 20 Sorbitan Monooleate | emulsifier | 0.6 |
| Isopropylamine alkyl benzene sulfonate | emulsifier | 1.7 |
| Water | diluent | 90.0 |

| Ingredient | Purpose | wt. % |
|---|---|---|
| 3C | active ingredient | 5.0 |
| Caster oil (40 mol EO) | emulsifier | 2.7 |
| POE 20 Sorbitan Moncoleate | emulsifier | 0.6 |
| Isopropylamine alkyl benzene sulfonate | emulsifier | 1.7 |
| Water | diluent | 90.0 |

The individual chemicals of the present invention and mixtures may also be used as an aerosol spray. While not limited thereto, the following formulation is typical:

| Ingredient | Purpose | wt. % |
|---|---|---|
| 3C | active ingredient | 5.0 |
| Propanol | solubilizing agent | 1.5 |

-continued

| Ingredient | Purpose | wt. % |
|---|---|---|
| Carbon dioxide | propellant | 3.5 |
| Isoparaffinic hydrocarbon | solvent | 90.0 |

A pesticidal shampoo has the following composition where the active ingredient is an individual chemical of the present invention or mixture of chemicals:

| Ingredient | wt. % |
|---|---|
| Active ingredient | 0.5–10.0 |
| Sequestrant for hard water | 0.5–3.0 |
| Emulsifier(s) | 1.0–5.0 |
| Thickener(s) | 0.5–5.0 |
| Foam stabilizer | 0.5–2.0 |
| Detergent | 5.0–20.0 |
| Buffer | 0.1–2.0 (to required pH) |
| Dye/colorant | 0.01 |
| Preservative | 0.01–1.0 |
| Deionized water | to 100% |

Gel formulations have been prepared as follows:

| | |
|---|---|
| 3.00% | Active ingredient |
| 15.00% | Ethanol |
| 0.42% | Carbopol 934 |
| 0.42%–10% | Sodium hydroxide in water |
| 81.16% | Water |

| | |
|---|---|
| 3.00% | Active ingredient |
| 30.00% | Ethanol |
| 0.42% | Carbopol 934 |
| 0.42%–10% | Sodium hydroxide in water |
| 66.16% | Water |

The active ingredient is an individual chemical of the present invention or a mixture thereof.

A dry powder formulation consists of mixing an alkaline earth metal carbonate, such as calcium carbonate, an alkali metal bicarbonate, such as sodium bicarbonate, the active ingredient, an absorbent material, such as diatomaceous earth and a bulk agent such as HiSil 233.

The relative concentrations of the mixture are preferably about 20%–30% alkaline earth metal carbonate, 15%–25% alkali metal bicarbonate, 0.1%–5% active ingredient, 30%–50% absorbent material and 5%–15% bulk agent (all by weight). The granules of powder preferably are ground to a size under 100 microns.

The active ingredients may be individual chemicals of the present invention or mixtures thereof.

In all of the above recited examples, it may be desirable to add a trace amount (less than 2%) of a material to provide a pleasant odor, not only for aesthetic reasons but also to identify the areas of a building which have been treated. The pleasant odor may be vanilla, cinnamon, floral or other odors which are acceptable to consumers. The pleasant odors are not limited to the examples given herein.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A contact pesticide for invertegrates including cockroaches, army worms, fire ants and spider mites consisting of:

an affector agent composed of carbon, hydrogen and oxygen atoms, the affector agent being a mixture selected from a group consisting of (a) a blend of cinnamic alcohol, engenol with alpha terpineol; (b) a blend of benzyl alcohol, phenyl ethyl alcohol, eugenol with alpha terpineol; (c) and a blend of benzyl acetate, benzyl alcohol, phenyl ethyl alcohol, cinnamic alcohol with alpha terpineol, the affector agent blocking octopamine receptor sites in the cockroaches, army worms, fire ants and spider mites, an inert carrier in which the affector agent is intimately mixed, the affector agent being present in the pesticide in an effective amount to interact as an agonist or antagonist on the octopamine receptor sites, wherein exposure of the cockroaches, army worms, fire ants and spider mites to the affector agent interferes with neurotransmission and causes the death of the exposed cockroaches, army worms, fire ants and spider mites.

2. The pesticide of claim 1, wherein the affector agent is approximately 0.1%–10% by weight.

3. The pesticide of claim 1, wherein each blend is an equal part by weight of the respective components.

4. A contact pesticide consisting of an inert carrier and an affector agent, the affector agent interfering with neurotransmission in cockroaches, army worms, fire ants and spider mites, the affector agent being a mixture selected from the group consisting of (a) a blend of cinnamic alcohol, eugenol and alpha terpineol; (b) a blend of benzyl alcohol, phenyl ethyl alcohol, eugenol and alpha terpineol; and (c) a blend of benzyl acetate, benzyl alcohol, phenyl ethyl alcohol, cinnamic alcohol and alpha terpineol, wherein the affector agent is approximately 0.1%–10% by weight.

5. A composition for controlling feeding damage caused by larvae, the composition consisting of:

a mixture of affector agents selected from the group consisting of (a) a blend of α-terpineol, eugenol and cinnamic alcohol, (b) a blend of phenyl ethyl alcohol, benzyl alcohol, eugenol and α-terpineol and (c) a blend of benzylacetate, benzyl alcohol, phenyl ethyl alcohol, cinnamic alcohol and α-terpineol, an inert carrier, the mixture and the carrier being combined, thereby forming a concentrate, the mixture being approximately 90% by weight and the carrier being approximately 10% by weight the concentrate being diluted with water to a desired dilution, wherein exposure of the larvae to the diluted composition reduces feeding damage caused by the exposed larvae to less than 30% area consumed as compared to 80% area consumed caused by unexposed larvae.

6. The composition of claim 5, wherein the concentrate is diluted 50 to 1 and the area consumed is less than 5%.

7. The composition of claim 5, wherein the concentrate is diluted 70 to 1 and the area consumed is less than 30%.

* * * * *